United States Patent [19]

Bezborodov et al.

[11] Patent Number: 4,853,150
[45] Date of Patent: Aug. 1, 1989

[54] 2-(4,3-DISUBSTITUTED PHENYL)-5-ALKYL-1,3,2-DIOXABORINANE DERIVATIVES AND LIQUID CRYSTAL MATERIAL

[75] Inventors: Vladimir S. Bezborodov; Oleg A. Grinkevich, both of Minsk; Mikhail F. Grebenkin, Moscow; Valery I. Lapanik, Minsk; Anatoly A. Minko, Minsk; Vitaly V. Rzhussky, Minsk; Anatoly A. Muravsky, Minsk; Vladimir F. Petrov, Moscow; Alexandr V. Ivaschenko, Minsk, all of U.S.S.R.

[73] Assignee: Nauchno-Issledovatelsky Institut Prikladnykh Fizicheskikh Problem Imeni A. N. Sevchenko, Minsk, U.S.S.R.

[21] Appl. No.: 133,635

[22] Filed: Dec. 16, 1987

[30] Foreign Application Priority Data

Dec. 17, 1986 [SU] U.S.S.R. .............. 4162761[I]
Dec. 17, 1986 [SU] U.S.S.R. .............. 4162762[I]
Mar. 17, 1987 [SU] U.S.S.R. .............. 4206873[I]
Mar. 17, 1987 [SU] U.S.S.R. .............. 4206874[I]
Mar. 17, 1987 [SU] U.S.S.R. .............. 4206875[I]

[51] Int. Cl.$^4$ .................. C09K 19/34; G02F 1/13; C07F 5/04
[52] U.S. Cl. .................. 252/299.61; 252/299.5; 350/350 R; 350/350 S; 558/288
[58] Field of Search .................. 252/299.61, 299.5; 558/288; 350/350 R, 350 S

[56] References Cited

U.S. PATENT DOCUMENTS 4,751,017 6/1988 Wachtler et al. .............. 252/299.61

FOREIGN PATENT DOCUMENTS 61-83190 4/1986 Japan .............. 252/299.61
61-10972 5/1986 Japan .............. 252/299.61
61-97293 5/1986 Japan .............. 252/299.61

OTHER PUBLICATIONS

Synthese und Eigenshaften Substituierter 1,3-Dioxane, J. Prakt. Chemie, vol. 323, H. M. Vorbrodt et al, pp. 903-913, (1981).

Primary Examiner—Teddy S. Gron
Attorney, Agent, or Firm—Ladas & Parry

[57] ABSTRACT 2-(4,3-Disubstituted phenyl)-5-alkyl-1,3,2-dioxaborinane derivatives of the general formula

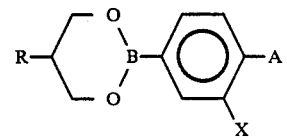

wherein A is —OR', —CN,

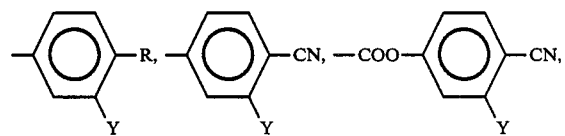

X,Y being simultaneously or independently H, F, Cl, R, R' standing for an alkyl radical of a normal structure, comprising from 1 to 7 carbon atoms, as components for a liquid crystal material. A liquid crystal material comprises at least two components, of which one is a compound of said formula, taken in an amount of from 3 to 75 percent by mass.

13 Claims, No Drawings

2-(4,3-DISUBSTITUTED PHENYL)-5-ALKYL-1,3,2-DIOXABORINANE DERIVATIVES AND LIQUID CRYSTAL MATERIAL

FIELD OF APPLICATION

The present invention relates to novel organic compounds possessing liquid-crystal properties and, more particularly, to 2-(4,3-disubstituted phenyl)-5-alkyl-1,3,2-dioxaborinane derivatives as components of a liquid crystal material and to a liquid crystal material for use in electrooptical devices.

The present invention will find extensive application in the electronic industry for the presentation of alpha-numeric information, for instance, in electronic watches and microcalculators.

BACKGROUND OF THE INVENTION

Known in the art are liquid crystalline trans-2-[4-(4'-cyanophenyloxycarbonyl)phenyl]-5-alkyl-1,3-dioxanes of the formula

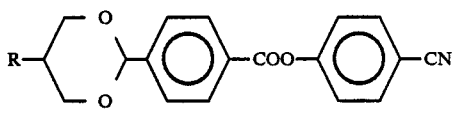

wherein R is an alkyl radical of a normal structure with 6 or 7 carbon atoms (J. für prakt. Chem., Bd. 323, No. 6, 1981, Leipzig, H. M. Vorbrodt, S. Deresch, H. Kresse, A. Wiegeleben, D. Denues, H. Laschke, "Synthese and Eigenschaften substituierter 1,3-Dioxane", S. 902–13).

These compounds are characterized by high temperatures of nematic phase formation (135° C.) and by a liability to isomerization to corresponding cis-isomers, whereas liquid crystal materials based on these compounds are inadequate in terms of their electrooptical parameters and cannot be used in the range of negative temperatures.

Also known in the art are 2-(4-substituted phenyl)-5-alkyl-1,3,2-dioxaborinanes of the formula

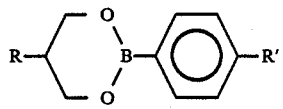

wherein R is an alkyl radical of a normal structure, comprising from 3 to 6 carbon atoms; R' is —OR, —CN,

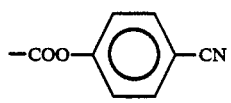

(JP, A, NOS. 61-83190, 61-109792).

These compounds have a rather high temperature of nematic phase formation (not lower than 105° C.) and a low positive anisotropy of permittivity. As a result, the threshold voltage and saturation voltage of the "twist"-effect of the liquid crystal material comprising these compounds are high, and the material becomes inapplicable at low temperatures.

BRIEF DESCRIPTION OF THE INVENTION

It is an object of the present invention to provide novel 2-(4,3-disubstituted phenyl)-5-alkyl-1,3,2-dioxaborinane derivatives as components of a liquid crystal material, featuring low values of the nematic phase formation temperature and high values of the positive anisotropy of permittivity, as well as to provide a liquid crystal material characterized by low values of the threshold voltage and saturation voltage, and also by short ON and OFF periods.

The object of the invention is accomplished by the provision of 2-(4,3-disubstituted phenyl)-5-alkyl-1,3,2-dioxaborinanes of the general formula

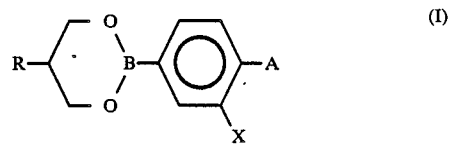

wherein A is —OR, —CN

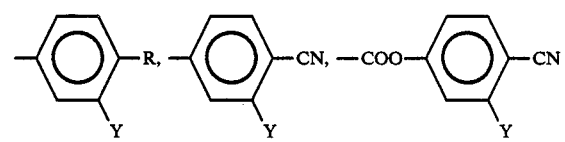

X,Y being simultaneously or independently H, F, Cl, R, R' standing for an alkyl radical of a normal structure, comprising from 1 to 7 carbon atoms, as components for a liquid crystal material.

It is also recommendable to use derivatives of 2-(4,3-disubstituted phenyl)-5-alkyl-1,3,2-dioxaborinanes of the formulas

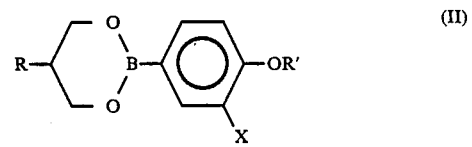

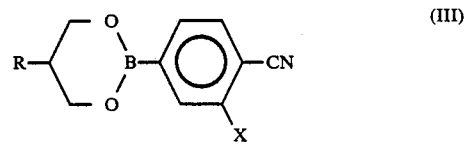

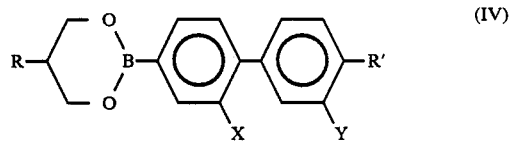

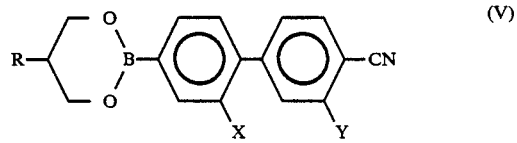

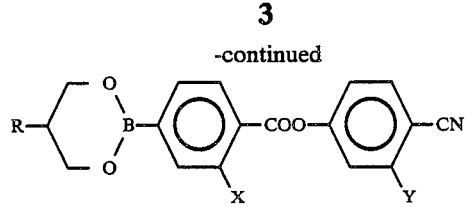

A liquid crystal material is also proposed, comprising at least two components, wherein, according to the invention, at least one of said components is the herein-proposed 2-(4,3-disubstituted pheny)-5-alkyl-1,3,2-dioxaborinane derivative of the formula (I)–(VI).

It is expedient that the content of the herein-proposed compounds of the formulas (I)–(VI) in the liquid crystal material should be 3–75 percent by mass.

Such liquid crystal materials are characterized by optimal properties.

DETAILED DESCRIPTION OF THE INVENTION

The compounds of the formula (I)–(VI), according to the invention, feature low values of the nematic phase formation temperatures and high values of the positive anisotropy of permittivity. These properties make the liquid crystal material comprising such compounds suitable for use in the range of low temperatures, secure low values of its threshold voltage and saturation voltage, a steep voltage-contrast characteristic, short ON and OFF periods.

The liquid crystal materials according to the invention will find application in various electrooptical devices with static and dynamic control modes in devices operating in a multiplex mode, for instance, in electronic wathces, microcalculators, television screens, in personal computers, and the like.

Given hereinbelow is a method of synthesizing the compounds of the formulas (I)–(VI).

The compounds of the formulas (II), (IV) are prepared by reacting 2-alkyl-1,3-propanediols with a 4,3-disubstituted phenylboric acid in acetone.

A reaction of 2-alkyl-1,3-propanediols with 4-carboxy-3-halogenophenylboric acid and a subsequent treatment of the reaction product with thionyl chloride give an acid chloride which, by means of a conventional method is converted successively into an amide and nitrile (III); a compound of the formula (VI) is synthesized by means of 4-hydroxybenzonitrile, 4-hydroxy-2-halogenobenzonitrile in the medium of pyridine. A compound of the formula (V) is prepared in a similar manner, as in the case of the compound of the formula (IV), by using 4-carboxy-3,2'-disubstituted 4-diphenylboric acid.

A liquid crystal material, according to the invention, is prepared by mixing at least two components, of which one is, according to the invention, a 2-(4,3-disubstituted phenyl)-5-alkyl-1,3,2-dioxaborinane derivative, taken in an amount of 3–75 percent by mass. The mixing is effected under heating till the appearance of an isotropic phase, and is followed by cooling.

The other component of the liquid crystal material may be any compound selected from the classes of: derivatives of biphenyl, cyclohexane, dioxanes, pyrimidine, alkyl(alkoxy)phenyl esters, 4-alkyl(alkoxy)benzoic acids and trans-4-alkyl-cyclohexanecarboxylic acids, alkylphenyl esters of 4-(trans-4-alkylcyclohexyl) benzoic acids, 4-(trans-4-alkylcyclohexyl)phenyl esters of trans-4-alkylcyclohexanecarboxylic acids, 1,2-diphenylethane, 1-cyclohexyl-2-phenylethane.

Given hereinbelow are examples of specific embodiments of the present invention, Examples 1–5 illustrating the methods of preparing and the properties of the 2-(4,3-disubstituted phenyl)-5-alkyl-1,3,2-dioxaborinane derivatives of the formulas (II)–(VI), Examples 6–9 illustrating the method of preparing and the properties of the liquid crystal material.

EXAMPLE 1

Preparing of 2-(4-phentyloxy-3-chlorophenyl)-5-pentyl-1,3,2-dioxaborinane (II)

A mixture comprising 0.02 mole of 2-pentyl-1,3-propanediol, 0.02 mole of 4-pentyloxy-3-chlorophenylboric acid in 50 ml of acetone is refluxed for 1–1.5 hour. The solvent is distilled off, the resulting product is recrystallized from a minimal quantity of acetone (by freezing out).

The yield of the compound (II) is 53% M.p. 8° C. Other compounds of the formula (II) with the number of carbon atoms in the alkyl radicals from 1 to 7 and with X standing for H, F, Cl atoms are prepared in a similar manner, their yield being 50–72%.

EXAMPLE 2

Preparing of 2-(4-cyano-3-fluorophenyl)-5-pentyl-1,3,2-dioxaborinane (III)

A mixture comprising 0.025 mole of 4-carboxy-3-fluorophenylboric acid, 0.025 mole of 2-pentyl-1,3-propanediol in 70 ml of acetone is refluxed for 5 hours. The solvent is distilled off, the product is crystallized from methyl ethyl ketone. The resulting 2-(4-carboxy-3-fluorophenyl)-5-pentyl-1,3,2-dioxaborinane in an amount of 0.02 mole is refluxed with 5 ml of thionyl chloride for 1 hour. The residue, after distilling off excess thionyl chloride, is treated with 15 ml of an aqueous solution of ammonia. The precipitated crystals are filtered off, washed with water, dried in air, and then placed into a solution comprising 10 ml of dimethylformamide and 0.8 ml of thionyl chloride. In this solution the crystals are kept for 1 hour, then the solution with the crystals is poured into an aqueous solution of sodium bicarbonate and extracted with diethyl ether. The ethereal solution is washed with water and dried with anhydrous sodium sulphate. The residue obtained after distilling off the solvent is recrystallized from methyl alcohol (by freezing out).

The yield of the compound (III) is 45%. M.p. 29° C. Other compounds of the formula (III) with the number of carbon atoms in the alkyl radical from 1 to 7 and X standing for F, Cl atoms were prepared in a similar manner, their yield being 45–57%.

EXAMPLE 3

Preparing of 2-(4-ethyl-3-fluoro-4'-diphenyl)-5-pentyl-1,3,2-dioxaborinane (IV)

A mixture comprising 0.02 mole of 2-pentyl-1,3-propanediol, 0.02 mole of 4-alkyl-3-fluoro-4'-diphenylboric acid in 100 ml of acetone is refluxed for 3–4 hours. The solvent is distilled off, the resulting product is recrystallized from a minimal quantity of acetone.

The yield of the compound (IV) is 53%. M.p. 87° C.

Other compounds of the formula (IV) with the number of carbon atoms in the alkyl radicals from 1 to 7 and X, Y standing for H, F, Cl atoms were prepared in a similar manner, the yield thereof being 45-59%.

EXAMPLE 4

Preparing of 2-(4-cyano-3,2'-difluoro-4'-diphenyl-5-pentyl-dioxaborinane (V)

A mixture comprising 0.02 mole of 2-pentyl-1,3-propanediol, 0.02 mole of 4-carboxy-3,2'-difluoro-4'-diphenylboric acid in 120 ml of acetone is refluxed for 10 hours. The solvent is distilled off, the product is crystallized from toluene. The resulting 2-(4-carboxy-3,2'-difluoro-4'-diphenyl)-5-pentyl-1,3,2-dioxaborinane in an amount of 0.015 mole is refluxed with 7 ml of thionyl chloride for 3 hours. The residue, after distilling off excess thionyl chloride, is dissolved in dioxane and treated with 15 ml of aqueous ammonia. The precipitated crystals are filtered off, washed with water, dried in air, then placed into a solution of 35 ml of dimethylformamide and 3 ml thionyl chloride. The solution is allowed to stand for 4 hours, then it is poured into an aqueous solution of sodium bicarbonate and extracted with diethyl ether. The ethereal solution is washed with water and dried with anhydrous sodium sulphate. The residue obtained after distilling off the solvent is recrystallized from a mixture of hexane with isopropyl alcohol.

The yield of the compound (V) is 36%. M.p. 62° C.

Other compounds of the formula (V) with the number of carbon atoms in the alkyl radical from 1 to 7 and X, Y standing for H, F, Cl atoms were prepared in a similar manner, the yield thereof being 33-42%.

EXAMPLE 5

Preparing of 2-[4'-(4-cyano-3-fluorophenyloxycarbonyl)-3'-fluorophenyl]-5-pentyl-1,3,2-dioxaborinane (VIs)

A mixture comprising 0.025 mole of 4-carboxy-3-fluorophenylboric acid, 0.025 mole of 2-pentyl-1,3-propanediol in 70 ml of acetone is boiled in a flask with a reflux condenser for 5 hours. The solvent is distilled off, the product is crystallized from methyl ethyl ketone.

A mixture comprising 0.004 mole of 2-(4-carboxy-3-flurophenyl)-5-pentyl-1,3,2-dioxaborinane, 0.32 ml of pyridine, 0.32 ml of thionyl chloride in 50 ml of anhydrous diethyl ether is stirred for 1 hour. Then 0.004 mole of 4-hydroxy-2-fluorobenzonitrile and 1 ml of pyridine are added. The mixture is allowed to stand overnight and then filtered. The residue obtained after distilling off the solvent is crystallized from a mixture of hexane and ethyl alcohol. The yield of the compound (VIs) is 60%. M.p. 63° C.

Other compounds of the formula (VIa-w) were obtained in a similar manner, their yield being 47-86%. The properties, yields, and elemental analysis of the compounds (VIa-w) are presented in Table 1.

TABLE 1

$$R-\underset{O}{\overset{O}{\diagup}}B-\bigcirc-COO-\bigcirc-CN$$

| Nos. 1 | R 2 | X 3 | Y 4 | Yield % 5 | Temperature range of nematic phase existence °C. or m.p. °C. 6 | Found, % C 7 | H 8 | B 9 |
|---|---|---|---|---|---|---|---|---|
| a | $C_3H_7$ | F | H | 67 | 89-174 | 65.61 | 5.27 | 3.08 |
| b | $C_3H_7$ | Cl | H | 51 | 109-114 | 62.73 | 5.11 | 3.04 |
| c | $C_4H_9$ | F | H | 76 | 95-168 | 65.98 | 5.28 | 2.67 |
| d | $C_5H_{11}$ | F | H | 64 | 94-167 | 66.64 | 6.06 | 2.77 |
| e | $C_5H_{11}$ | Cl | H | 68 | 93-109 | 64.43 | 5.40 | 2.51 |
| f | $C_6H_{13}$ | F | H | 72 | 97-157 | 67.70 | 6.34 | 2.82 |
| g | $C_7H_{15}$ | F | H | 65 | 95-153 | 68.33 | 6.18 | 2.65 |
| h | $C_3H_7$ | H | F | 75 | 126-173.5 | 65.70 | 5.25 | 3.03 |
| i | $C_3H_7$ | F | F | 83 | 103-143.5 | 63.62 | 4.91 | 2.97 |
| j | $C_3H_7$ | Cl | F | 72 | 78 | 59.64 | 4.35 | 2.81 |
| k | $C_3H_7$ | F | Cl | 86 | 111 | 60.02 | 4.29 | 2.46 |
| l | $C_4H_9$ | H | F | 57 | 103-164 | 66.31 | 5.42 | 2.90 |
| m | $C_4H_9$ | H | Cl | 58 | 115-116 | 62.34 | 5.01 | 2.47 |
| n | $C_4H_9$ | F | Cl | 74 | 104 | 60.90 | 4.58 | 2.78 |
| o | $C_4H_9$ | F | F | 79 | 64-143 | 64.32 | 4.97 | 2.75 |
| p | $C_5H_{11}$ | H | F | 47 | 82-109 | 66.73 | 5.66 | 2.93 |
| q | $C_5H_{11}$ | H | Cl | 62 | 106-117 | 63.15 | 5.22 | 2.50 |
| r | $C_5H_{11}$ | F | Cl | 68 | 105 | 61.27 | 5.34 | 2.28 |
| s | $C_5H_{11}$ | F | F | 60 | 63-142 | 65.04 | 5.62 | 2.51 |
| t | $C_5H_{11}$ | Cl | F | 73 | 59-74 | 61.71 | 5.33 | 2.36 |
| u | $C_5H_{11}$ | Cl | Cl | 73 | 86 | 57.96 | 4.94 | 2.15 |
| v | $C_6H_{13}$ | F | F | 62 | 68-131 | 64.60 | 5.52 | 2.53 |
| w | $C_7H_{15}$ | F | F | 57 | 71-131 | 65.48 | 6.17 | 2.27 |

| Nos. T 1 | Formula 10 | Calculated, % C 11 | H 12 | B 13 |
|---|---|---|---|---|
| a | $C_{20}H_{19}BFNO_4$ | 65.43 | 5.18 | 2.94 |
| b | $C_{20}H_{19}BClNO_4$ | 62.62 | 4.96 | 2.82 |
| c | $C_{21}H_{21}BFNO_4$ | 66.18 | 5.51 | 2.84 |
| d | $C_{22}H_{23}BFNO_4$ | 66.87 | 5.83 | 2.74 |
| e | $C_{22}H_{23}BClNO_4$ | 64.19 | 5.59 | 2.62 |
| f | $C_{23}H_{25}BFNO_4$ | 67.51 | 6.11 | 2.64 |
| g | $C_{24}H_{27}BFNO_4$ | 68.12 | 6.39 | 2.55 |
| h | $C_{20}H_{19}BFNO_4$ | 65.43 | 5.18 | 2.94 |

TABLE 1-continued

| | | | | |
|---|---|---|---|---|
| i | $C_{20}H_{18}BF_2NO_4$ | 63.73 | 4.78 | 2.87 |
| j | $C_{20}H_{18}BFClNO_4$ | 59.81 | 4.49 | 2.69 |
| k | $C_{20}H_{18}BFClNO_4$ | 59.81 | 4.49 | 2.69 |
| l | $C_{21}H_{21}BFNO_4$ | 66.18 | 5.51 | 2.83 |
| m | $C_{21}H_{21}BClNO_4$ | 62.15 | 5.18 | 2.66 |
| n | $C_{21}H_{20}BFClNO_4$ | 60.69 | 4.82 | 2.60 |
| o | $C_{21}H_{20}BF_2NO_4$ | 64.51 | 5.12 | 2.76 |
| p | $C_{22}H_{23}BFNO_4$ | 66.87 | 5.83 | 2.74 |
| q | $C_{22}H_{23}BClNO_4$ | 62.94 | 5.48 | 2.57 |
| r | $C_{22}H_{22}BFClNO_4$ | 61.50 | 5.12 | 2.52 |
| s | $C_{22}H_{22}BF_2NO_4$ | 65.25 | 5.44 | 2.67 |
| t | $C_{22}H_{22}BFClNO_4$ | 61.50 | 5.12 | 2.52 |
| u | $C_{22}H_{22}BCl_2NO_4$ | 58.16 | 4.87 | 2.38 |
| v | $C_{23}H_{24}BF_2NO_4$ | 64.67 | 5.62 | 2.53 |
| w | $C_{24}H_{26}BF_2NO_4$ | 65.34 | 5.90 | 2.45 |

All the novel compounds of the formulas (I)–(VIa–w) are at room temperature a white crystalline powder.

The composition and structure of the compounds (I)–(VIa–w) are confirmed by the results of the elemental analysis and the IR-, PMR-spectroscopy data.

Thus, in the PMR spectra of the 1,3,2-dioxaborinane derivatives (I)–(VI) (10% solution in deuteroacetone, standard-hexamethyldisiloxane, δ, ppm) signals due to the hydrogen atoms of the borinane fragment are observed in the region of 3.4–4.3 (centres at 3.54, 3.70, 3.86, 4.00, 4.10, 4.16, 4.26 or 3.53, 3.63, 3.74, 3.93, 4.00, 4.13, 4.20). Signals due to the hydrogen atoms of the benzene rings are observed in the region of 7.10–8.06 ppm. In the IR spectra of the compounds (0.1 molar solutions in $CCl_4$, chloroform) intensive peaks of 1715, 2215 $cm^{-1}$ correspond to the stretching vibrations of the carbonyl of the ester fragment, nitrile group.

Comparative data on the temperatures of nematic phase formation, positive anisotropy of permittivity for the compounds (VIa–f, i, s) according to the invention and for the compounds disclosed in Application JP, A, No. 61-109792 are presented in Table 2.

TABLE 2

| Compounds (VI) according to the invention, of the formula | | | | | | Compounds disclosed in Application JP, A, 61-83190, of the formula | | |
|---|---|---|---|---|---|---|---|---|
| VI | R | X | Y | Δε | Temperature of nematic phase formation, °C. | R | Δε | Temperature of nematic phase formation, °C. |
| 1 | 2 | 3 | 4 | 5 | 6 | 7 | 8 | 9 |
| a | $C_3H_7$ | F | H | 38 | 89 | $C_3H_7$ | 31.5 | 105 |
| b | $C_3H_7$ | Cl | H | 29 | 109 | $C_4H_9$ | 24 | 121 |
| c | $C_4H_9$ | F | H | 31.5 | 95 | $C_5H_{11}$ | 18.5 | 127 |
| d | $C_5H_{11}$ | F | H | 26 | 94 | $C_6H_{13}$ | 14.5 | 123 |
| f | $C_6H_{13}$ | F | H | 22 | 97 | | | |
| i | $C_3H_7$ | F | F | 90 | 83 | | | |
| s | $C_5H_{11}$ | F | F | 77 | 63 | | | |

Δε— is the positive anisotropy of permittivity, measured at the temperature 60° C. below the temperature of transition from the nematic phase to isotropic liquid.

From Table 2 it is apparent that the novel compounds (VI) have lower values of the nematic phase formation temperature and considerably higher values of the positive anisotropy of permittivity than similar compounds disclosed in Application JP, A, No. 61-109792.

For comparing the herein-proposed compounds of the mulas (III), (IV) and the compounds disclosed in Applications JP, A, No. 61-109792 and JP, A, No. 61-83190, mixtures were prepared, consisting of 15 percent by mass of said compounds and 85 percent by mass of a mixture of composition A. The mixture of composition A comprises 66 percent by mass of 4-butyl-methoxyanizole and 34 percent by mass of 4-butyl-4-hexylcarboxyazoxybenzene. The results on the positive anisotropy of permittivity of the prepared mixtures are presented in Tables 3, 4.

TABLE 3

Mixture incorporating:

R—⟨O-B-O⟩—⟨phenyl(X)⟩—COO—⟨phenyl(Y)⟩—CN (VI)

Mixture incorporating:

R—⟨O-B-O⟩—⟨phenyl⟩—COO—⟨phenyl⟩—CN (JP, A 61-83190)

| VI | R | X | J | Δε | R | Δε |
|---|---|---|---|---|---|---|
| a | $C_3H_7$ | F | H | 8.0 | $C_4H_9$ | 4.7 |
| h | $C_3H_7$ | H | F | 7.9 | | |
| i | $C_3H_7$ | F | F | 15.8 | | |
| j | $C_3H_7$ | Cl | F | 9.8 | $C_3H_7$ | 6.2 |
| k | $C_3H_7$ | F | H | 11.2 | | |
| m | $C_4H_7$ | H | Cl | 6.6 | | |
| n | $C_4H_9$ | F | Cl | 8.3 | | |
| o | $C_4H_9$ | F | F | 12.5 | | |
| p | $C_5H_{11}$ | H | F | 5.0 | $C_5H_{11}$ | 3.8 |
| q | $C_5H_{11}$ | H | Cl | 4.7 | | |
| r | $C_5H_{11}$ | F | Cl | 7.2 | | |
| s | $C_5H_{11}$ | F | F | 10.8 | | |
| t | $C_5H_{11}$ | Cl | F | 7.8 | | |
| u | $C_5H_{11}$ | Cl | Cl | 5.7 | | |

TABLE 4

Mixture incorporating:

R—⟨O-B-O⟩—⟨phenyl(X)⟩—CN (III)

Mixture incorporating:

R—⟨O-B-O⟩—⟨phenyl⟩—CN (JP, A 61-109792)

| R | X | Δε | R | Δε |
|---|---|---|---|---|
| 1 | 2 | 3 | 4 | 5 |
| $C_3H_7$ | F | 6.1 | | |
| $C_3H_7$ | Cl | 5.9 | $C_3H_7$ | 5.7 |
| $C_5H_{11}$ | F | 4.7 | $C_5H_{11}$ | 4.2 |

EXAMPLE 6

A mixture is prepared, comprising 20 percent by mass of 4-cyano-4'-pentyldiphenyl (VII), 10 percent by mass of 4-ethoxyphenyl ester of trans-4-butylocyclohexanecarboxylic acid (VIII), 30 percent by mass of 2-/4-(4-cyanophenyloxycarbonyl)phenyl/-5-pentyl-1,3-dioxane (IX), 15 percent by mass of ethylphenyl ester of trans-4-hexylcyclohexanecarboxylic acid (X), 10 percent by mass of ethoxyphenyl ester of 4-butylbenzoic acid (XI), and 15 percent by mass of 2-(4-cyano-3-fluorophenyl)-5-propyl-1,3,2-dioxaborinane (III). The mixture is heated till the appearance of isotropic phase, stirred, and cooled down to room temperature. The properties of the liquid crystal material thus obtained are presented in Table 5.

Liquid crystal materials of compositions Nos. 2–54 were prepared in a similar manner.

Their properties are also presented in Table 5.

TABLE 5

| Composition No. | Liquid crystal material | % by mass | Δε 20° C. | M.p., °C. | $T_{lim.}$, °C. |
|---|---|---|---|---|---|
| 1. | 2 | 3 | 4 | 5 | 6 |
| 1. | $C_5H_{11}$—⟨phenyl⟩—⟨phenyl⟩—CN (VII) | 20 | 9.8 | −10 | 72.1 |
| | $C_3H_7$—⟨O-B-O⟩—⟨phenyl(F)⟩—CN (III) | 15 | | | |
| | $C_4H_9$—⟨cyclohexyl⟩—COO—⟨phenyl⟩—$OC_2H_5$ (VIII) | 10 | | | |

TABLE 5-continued
| Composition No. 1. | Liquid crystal material 2. | | % by mass 3 | Δε 20° C. 4 | M.p., °C. 5 | T$_{lim.}$, °C. 6 |
|---|---|---|---|---|---|---|
| | 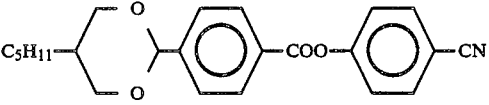 | (IX) | 30 | | | |
| | 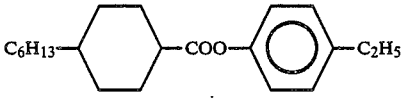 | (X) | 15 | | | |
| | 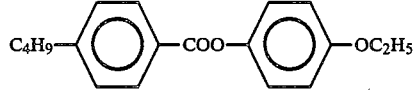 | (XI) | 10 | | | |
| 2. |  | (VII) | 20 | 12.04 | −7 | 64.5 |
| | 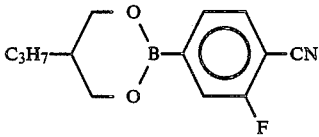 | (III) | 15 | | | |
| | 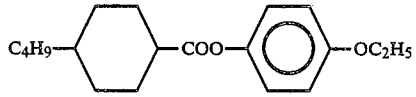 | (VIII) | 10 | | | |
| | 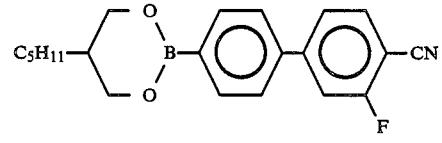 | (V) | 30 | | | |
| | 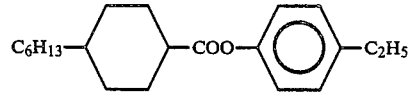 | (X) | 15 | | | |
| | 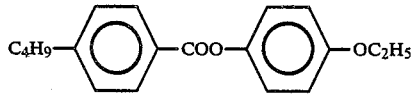 | (XI) | 10 | | | |
| 3. | YII | | 20 | 15.26 | −8 | 70.4 |
| | III | | 15 | | | |
| | YIII | | 10 | | | |
| | 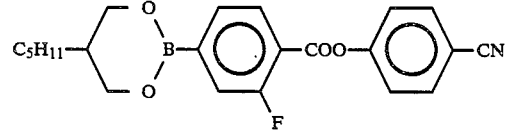 | (VId) | 30 | | | |
| | X | | 15 | | | |
| | XI | | 10 | | | |
| 4. | YII | | 20 | 11.96 | −6 | 67.4 |
| | III | | 15 | | | |
| | YIII | | 10 | | | |

TABLE 5-continued

| Composition No. | Liquid crystal material | | % by mass | Δε 20° C. | M.p., °C. | T$_{lim}$, °C. |
|---|---|---|---|---|---|---|
| 1. | 2 | | 3 | 4 | 5 | 6 |
| | C$_5$H$_{11}$—[boronate]—[phenyl(Cl)]—COO—[phenyl]—CN | (VIe) | 30 | | | |
| 5. | X | | 15 | | | |
| | XI | | 10 | | | |
| | YII | | 20 | 15.01 | −8 | 65.0 |
| | III | | 15 | | | |
| | YIII | | 10 | | | |
| 5. | C$_5$H$_{11}$—[boronate]—[phenyl]—COO—[phenyl(F)]—CN | (VIp) | 30 | | | |
| | X | | 15 | | | |
| | XI | | 10 | | | |
| 6. | YII | | 20 | 14.34 | −3 | 68.4 |
| | C$_5$H$_{11}$—[phenyl]—[phenyl]—CN | (VII) | | | | |
| | C$_3$H$_7$—[boronate]—[phenyl(F)]—CN | (III) | 15 | | | |
| | C$_4$H$_9$—[cyclohexyl]—COO—[phenyl]—OC$_2$H$_5$ | (VIII) | 10 | | | |
| | C$_5$H$_{11}$—[boronate]—[phenyl]—COO—[phenyl(Cl)]—CN | (VIg) | 30 | | | |
| | C$_6$H$_{13}$—[cyclohexyl]—COO—[phenyl]—C$_2$H$_5$ | (X) | 15 | | | |
| 6. | C$_4$H$_9$—[cyclohexyl]—COO—[phenyl]—OC$_2$H$_5$ | (XI) | 10 | | | |
| 7. | YII | | 20 | 29.76 | −12 | 70.4 |
| | III | | 15 | | | |
| | YIII | | 10 | | | |
| | C$_5$H$_{11}$—[boronate]—[phenyl(F)]—COO—[phenyl(F)]—CN | (VIs) | 30 | | | |
| | X | | 15 | | | |
| | XI | | 10 | | | |
| 8. | YII | | 20 | 20.06 | −7 | 59.4 |
| | III | | 15 | | | |
| | YIII | | 10 | | | |

TABLE 5-continued
| Composition No. | Liquid crystal material | | % by mass | Δε 20° C. | M.p., °C. | T_lim., °C. |
|---|---|---|---|---|---|---|
| 1. | 2 | | 3 | 4 | 5 | 6 |
| | 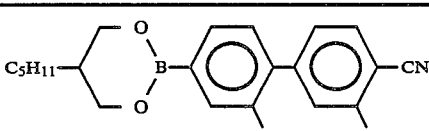 | (VIt) | 30 | | | |
| 9. | X<br>XI<br>YII<br>III<br>YIII | | 15<br>10<br>20<br>15<br>10 | 21.6 | −1 | 62.4 |
| | 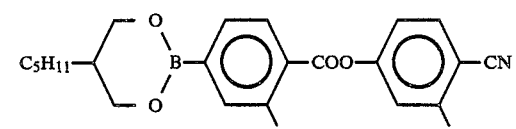 | (VIx) | 30 | | | |
| 10. | X<br>XI<br>YII<br>III<br>YIII | | 15<br>10<br>20<br>15<br>10 | 13.05 | 0 | 54.4 |
| | 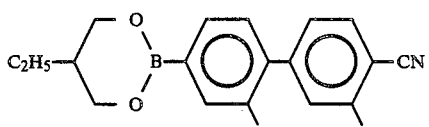 | (V) | 30 | | | |
| 11. | X<br>XI<br>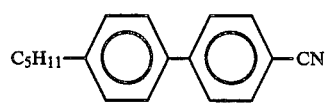 | (VII) | 15<br>10<br>15 | 8.25 | −18 | 72.1 |
| 11. | 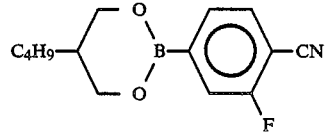 | (III) | 11 | | | |
| | 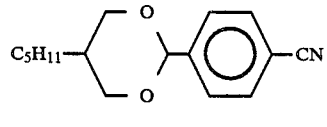 | (XII) | 9 | | | |
| | 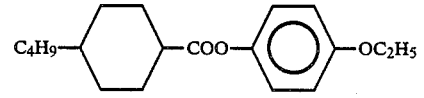 | (VIII) | 10 | | | |
| | 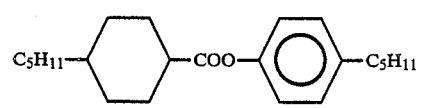 | (XIII) | 12 | | | |
| | 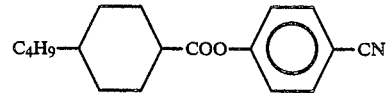 | (XIV) | 18 | | | |
| | 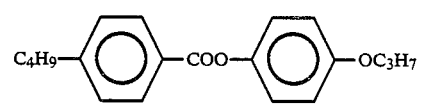 | (XV) | 10 | | | |

TABLE 5-continued

| Composition No. | Liquid crystal material | | % by mass | Δε 20° C. | M.p., °C. | $T_{lim.}$, °C. |
|---|---|---|---|---|---|---|
| 1. | 2 | | 3 | 4 | 5 | 6 |
|  | C$_3$H$_7$—[dioxaborinane]—[phenyl]—COO—[phenyl(F)]—CN | (VIn) | 8 | | | |
| 11. | C$_5$H$_{11}$—[dioxaborinane]—[phenyl(F)]—COO—[phenyl]—CN | (VId) | 7 | | | |
| 12. | YII | | 15 | 9.21 | −14 | 71.3 |
|  | III | | 11 | | | |
|  | XII | | 9 | | | |
|  | YIII | | 10 | | | |
|  | XIII | | 12 | | | |
|  | XIY | | 18 | | | |
|  | XY | | 10 | | | |
|  | C$_3$H$_7$—[dioxaborinane]—[phenyl(F)]—[phenyl]—CN | (V) | 8 | | | |
|  | C$_5$H$_{11}$—[dioxaborinane]—[phenyl(F)]—COO—[phenyl]—CN | (VId) | 7 | | | |
| 13. | YII | | 15 | 13.81 | −10 | 59.7 |
|  | III | | 11 | | | |
|  | XII | | 9 | | | |
|  | YIII | | 10 | | | |
|  | C$_5$H$_{11}$—[cyclohexyl]—COO—[phenyl]—C$_5$H$_{11}$ | (XIII) | 12 | | | |
| 13. | C$_4$H$_9$—[cyclohexyl]—COO—[phenyl]—CN | (XIV) | 18 | | | |
|  | C$_4$H$_9$—[phenyl]—COO—[phenyl]—OC$_3$H$_7$ | (XV) | 10 | | | |
|  | C$_3$H$_7$—[dioxaborinane]—[phenyl(F)]—COO—[phenyl]—CN | (VId) | 8 | | | |
|  | C$_2$H$_5$—[dioxaborinane]—[phenyl(F)]—COO—[phenyl]—CN | (VI) | 7 | | | |
| 14. | YII | | 15 | 8.28 | −15 | 62.0 |

TABLE 5-continued

| Composition No. | Liquid crystal material | | % by mass | Δε 20° C. | M.p., °C. | T$_{lim.}$, °C. |
|---|---|---|---|---|---|---|
| 1. | 2 | | 3 | 4 | 5 | 6 |
| | III | | 11 | | | |
| | XII | | 9 | | | |
| | YIII | | 10 | | | |
| | XIII | | 12 | | | |
| | XIY | | 18 | | | |
| | XY | | 10 | | | |
| | C$_3$H$_7$–[dioxaborinane]–[phenyl]–COO–[phenyl]–CN (with Cl) | (VIB) | 8 | | | |
| | C$_5$H$_{11}$–[dioxaborinane]–[phenyl]–[phenyl]–CN (with Cl) | (V) | 7 | | | |
| 15. | YII | | 15 | 10.78 | −17 | 63.2 |
| | III | | 11 | | | |
| | XII | | 9 | | | |
| | YIII | | 10 | | | |
| | XIII | | 12 | | | |
| | XIY | | 18 | | | |
| | XY | | 10 | | | |
| | C$_2$H$_5$–[dioxaborinane]–[phenyl]–[phenyl]–CN | (V) | 8 | | | |
| | C$_5$H$_{11}$–[dioxaborinane]–[phenyl]–COO–[phenyl]–CN (with F) | (VIp) | 7 | | | |
| 16. | C$_5$H$_{11}$–[phenyl]–[phenyl]–CN | (VII) | 15 | 13.47 | −15 | 65.1 |
| | C$_4$H$_9$–[dioxaborinane]–[phenyl]–CN (with F) | (III) | 11 | | | |
| | C$_5$H$_{11}$–[dioxane]–[phenyl]–CN | (XII) | 9 | | | |
| | C$_4$H$_9$–[cyclohexyl]–COO–[phenyl]–OC$_2$H$_5$ | (VIII) | 10 | | | |
| 16. | C$_5$H$_{11}$–[cyclohexyl]–COO–[phenyl]–C$_5$H$_{11}$ | (XIII) | 12 | | | |

TABLE 5-continued

| Composition No. | Liquid crystal material | | % by mass | Δε 20° C. | M.p., °C. | $T_{lim.}$, °C. |
|---|---|---|---|---|---|---|
| 1. | 2 | | 3 | 4 | 5 | 6 |
| | [C$_4$H$_9$–cyclohexyl–COO–phenyl–CN] | (XIV) | 18 | | | |
| | [C$_4$H$_9$–phenyl–COO–phenyl–OC$_3$H$_7$] | (XV) | 10 | | | |
| | [C$_3$H$_7$–dioxaborinane–phenyl(Cl)–COO–phenyl(F)–CN] | (VIk) | 8 | | | |
| | [C$_5$H$_{11}$–dioxaborinane–phenyl(Cl)–COO–phenyl(F)–CN] | (VIt) | 7 | | | |
| 17. | YII | | 15 | 15.25 | −21 | 53.4 |
| | III | | 11 | | | |
| | XII | | 9 | | | |
| | YIII | | 10 | | | |
| | XIII | | 12 | | | |
| | XIY | | 18 | | | |
| | XY | | 10 | | | |
| | [CH$_3$–dioxaborinane–phenyl(F)–COO–phenyl(Cl)–CN] | (VI) | 8 | | | |
| 17. | [C$_5$H$_{11}$–dioxaborinane–phenyl(Cl)–phenyl(F)–CN] | (V) | 7 | | | |
| 18. | YII | | 15 | 14.04 | −17 | 51.6 |
| | III | | 11 | | | |
| | XII | | 9 | | | |
| | YIII | | 10 | | | |
| | XIII | | 12 | | | |
| | XIY | | 18 | | | |
| | XY | | 10 | | | |
| | [C$_3$H$_{11}$–phenyl–phenyl–CN] | (V) | 8 | | | |
| | [C$_5$H$_{11}$–dioxaborinane–phenyl(F)–COO–phenyl(Cl)–CN] | (VIz) | 7 | | | |
| 19. | [C$_3$H$_{11}$–phenyl–phenyl–CN] | (VII) | 3 | 17.87 | −11 | 79.2 |

TABLE 5-continued
| Composition No. | Liquid crystal material | | % by mass | Δε 20° C. | M.p., °C. | T$_{lim.}$, °C. |
|---|---|---|---|---|---|---|
| | 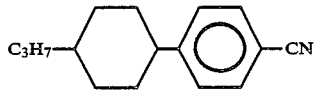 | (XVI) | 4 | | | |
| | 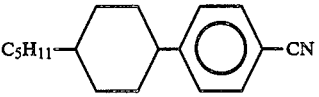 | (XVII) | 3 | | | |
| 19. | 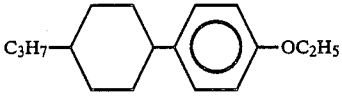 | (XVIII) | 5 | | | |
| | 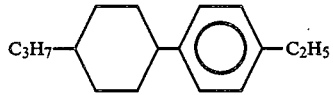 | (XIX) | 15 | | | |
| | 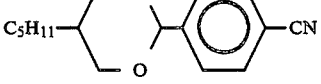 | (XII) | 6 | | | |
| | 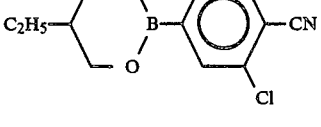 | (III) | 8 | | | |
| | 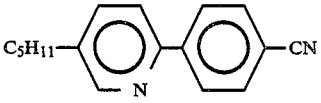 | (XX) | 3 | | | |
| |  | (XXI) | 5 | | | |
| | 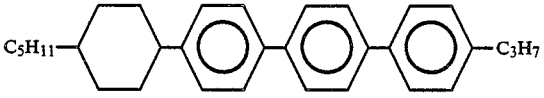 | (XXII) | 3 | | | |
| | 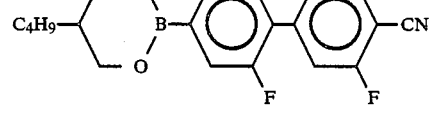 | (V) | 20 | | | |
| | 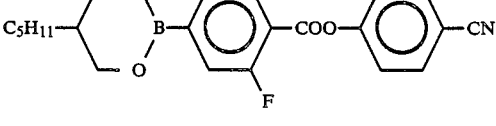 | (VId) | 25 | | | |
| 20. | YII | | 3 | 13.87 | −10 | 81.1 |
| | XYI | | 4 | | | |
| | XYII | | 3 | | | |
| | XYIII | | 5 | | | |
| | XIX | | 15 | | | |
| | XII | | 6 | | | |

TABLE 5-continued
| Composition No. | Liquid crystal material | | % by mass | Δε 20° C. | M.p., °C. | T$_{lim.}$, °C. |
|---|---|---|---|---|---|---|
| 1. | 2 | | 3 | 4 | 5 | 6 |
| | III | | 8 | | | |
| | XX | | 3 | | | |
| | XXI | | 5 | | | |
| | XXII | | 3 | | | |
| | 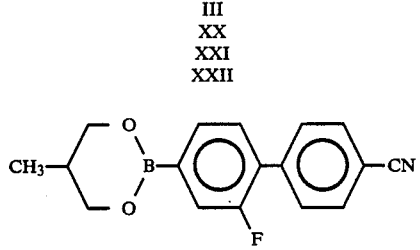 | (V) | 20 | | | |
| | 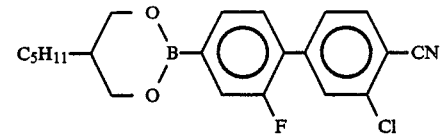 | (V) | 25 | | | |
| 21. | 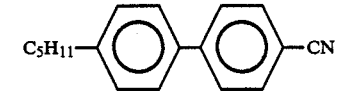 | (VII) | 3 | 12.12 | −12 | 71.4 |
| | 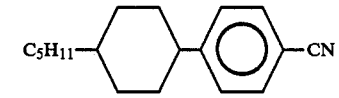 | (XVI) | 4 | | | |
| | 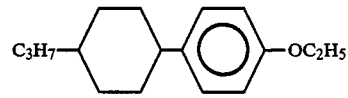 | (XVII) | 3 | | | |
| 21. | 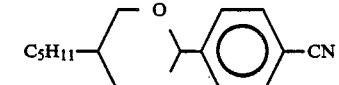 | (XVIII) | 5 | | | |
| | 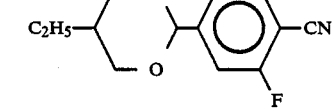 | (XIX) | 15 | | | |
| | 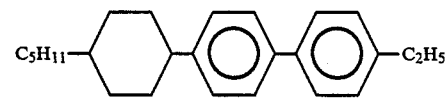 | (XII) | 6 | | | |
| |  | (III) | 8 | | | |
| |  | (XX) | 3 | | | |
| |  | (XXI) | 5 | | | |

TABLE 5-continued

| Composition No. | Liquid crystal material | | % by mass | Δε 20° C. | M.p., °C. | T$_{lim.}$, °C. |
|---|---|---|---|---|---|---|
| 1. | 2. | | 3 | 4 | 5 | 6 |
| | C$_5$H$_{11}$—[cyclohexyl]—[phenyl]—[phenyl]—[phenyl]—C$_3$H$_7$ | (XXII) | 3 | | | |
| | C$_2$H$_5$—[dioxaborinane]—[phenyl]—[phenyl(F)]—CN | (V) | 20 | | | |
| | C$_5$H$_{11}$—[dioxaborinane]—[phenyl]—[phenyl(F)]—CN | (V) | 25 | | | |
| 22. | YII | | 3 | 15.23 | −6 | 72.8 |
| | XYI | | 4 | | | |
| | XYII | | 3 | | | |
| | XYIII | | 5 | | | |
| | XIX | | 15 | | | |
| | XII | | 6 | | | |
| | III | | 8 | | | |
| | XX | | 3 | | | |
| | XXI | | 5 | | | |
| | XXII | | 3 | | | |
| | C$_4$H$_9$—[dioxaborinane]—[phenyl]—COO—[phenyl(F)]—CN | | | | | |
| | C$_5$H$_{11}$—[dioxaborinane]—[phenyl]—[phenyl(F)]—CN | (V) | 25 | | | |
| 23. | C$_5$H$_{11}$—[phenyl]—[phenyl]—CN | (VII) | 3 | 12.21 | −3 | 77.1 |
| | C$_3$H$_7$—[cyclohexyl]—[phenyl]—CN | (XVI) | 4 | | | |
| | C$_5$H$_{11}$—[cyclohexyl]—[phenyl]—CN | (XVII) | 3 | | | |
| 23. | C$_3$H$_7$—[cyclohexyl]—[phenyl]—OC$_2$H$_5$ | (XVIII) | 5 | | | |
| | C$_3$H$_{11}$—[cyclohexyl]—[phenyl]—C$_2$H$_5$ | (XIX) | 15 | | | |

TABLE 5-continued

| Composition No. | Liquid crystal material | | % by mass | Δε 20° C. | M.p., °C. | T$_{lim.}$, °C. |
|---|---|---|---|---|---|---|
| 1. | 2 | | 3 | 4 | 5 | 6 |
| | [structure with C$_2$H$_5$, dioxaborinane, biphenyl, CN, Cl] | (XII) | 6 | | | |
| | [structure with C$_2$H$_5$, dioxane, phenyl, CN, F] | (III) | 8 | | | |
| | [structure with C$_5$H$_{11}$, piperidine, phenyl, CN] | (XX) | 3 | | | |
| | [structure with C$_5$H$_{11}$, cyclohexyl, biphenyl, C$_2$H$_5$] | (XXI) | 5 | | | |
| | [structure with C$_5$H$_{11}$, cyclohexyl, terphenyl, C$_3$H$_7$] | (XXII) | 3 | | | |
| | [structure with C$_2$H$_5$, dioxaborinane, biphenyl, CN, F] | (V) | 20 | | | |
| | [structure with C$_5$H$_{11}$, dioxaborinane, phenyl-COO-phenyl, CN, Cl] | (VIg) | 25 | | | |
| 24. | YII | | 3 | 34.25 | −8 | 77.2 |
| | XYI | | 4 | | | |
| | XYII | | 3 | | | |
| | XYIII | | 5 | | | |
| | XIX | | 15 | | | |
| | XII | | 6 | | | |
| | III | | 8 | | | |
| | XX | | 3 | | | |
| | XXI | | 5 | | | |
| | XXII | | 3 | | | |
| | [structure with C$_4$H$_9$, dioxaborinane, phenyl-COO-phenyl, CN, F, F] | (V$_o$) | 20 | | | |
| | [structure with C$_2$H$_5$, dioxaborinane, biphenyl, CN, F, F] | (V) | 25 | | | |
| 25. | YII | | 3 | 22.07 | −2 | 64.1 |
| | XYI | | 4 | | | |
| | XYII | | 3 | | | |

TABLE 5-continued

| Composition No. | Liquid crystal material | | % by mass | Δε 20° C. | M.p., °C. | T$_{lim.}$, °C. |
|---|---|---|---|---|---|---|
| 1. | 2 | | 3 | 4 | 5 | 6 |
| | XYIII | | 5 | | | |
| | XIX | | 15 | | | |
| | XII | | 6 | | | |
| | III | | 8 | | | |
| | XX | | 3 | | | |
| | XXI | | 5 | | | |
| 25. | XXII | | 3 | | | |
| | $C_4H_9$—[dioxaborinane]—[phenyl(F)]—COO—[phenyl(Cl)]—CN | (VI$_n$) | 20 | | | |
| | $C_5H_{11}$—[dioxaborinane]—[phenyl(F)]—[phenyl(Cl)]—CN | (V) | 25 | | | |
| 26. | $C_5H_{11}$—[piperidine]—[phenyl]—CN | (XX) | 5 | 25.12 | −7 | 88.2 |
| | $C_3H_7$—[pyridyl]—[phenyl]—CN | (XXIII) | 5 | | | |
| | $C_5H_{11}$—[phenyl]—[pyridyl]—CN | (XXIV) | 5 | | | |
| | $C_7H_{15}$—[phenyl]—[pyridyl]—CN | (XXV) | 3 | | | |
| | $C_7H_{15}$—[phenyl]—[pyridyl]—CN | (VIII) | 5 | | | |
| | $C_6H_{13}$—[cyclohexyl]—COO—[phenyl]—$OC_2H_5$ | (X) | 5 | | | |
| 26. | $C_3H_7$—[cyclohexyl]—$CH_2CH_2$—[phenyl]—$OC_2H_5$ | (XXVI) | 10 | | | |
| | $C_5H_{11}$—[cyclohexyl]—[pyridyl]—[phenyl]—CN | (XXVII) | 2 | | | |

TABLE 5-continued

| Composition No. 1. | Liquid crystal material 2 | | % by mass 3 | Δε 20° C. 4 | M.p., °C. 5 | T<sub>lim.</sub>, °C. 6 |
|---|---|---|---|---|---|---|
| | [C$_3$H$_7$-dioxaborinane-phenyl(F)-COO-phenyl-CN] | (VIa) | 15 | | | |
| | [CH$_3$-dioxaborinane-phenyl-phenyl(Cl)-CN] | (V) | 15 | | | |
| | [C$_5$H$_{11}$-dioxaborinane-phenyl(F)-COO-phenyl-CN] | (VId) | 15 | | | |
| | [C$_6$H$_{13}$-dioxaborinane-phenyl-phenyl(F)-CN] | (V) | 15 | | | |
| 27. | XX | | 5 | 29.73 | −3 | 78.1 |
| | XXIII | | 5 | | | |
| | XXIY | | 5 | | | |
| | XXY | | 3 | | | |
| | VIII | | 5 | | | |
| | X | | 5 | | | |
| | XXYI | | 10 | | | |
| | XXYII | | 2 | | | |
| 27. | [C$_3$H$_7$-dioxaborinane-phenyl(F)-COO-phenyl(F)-CN] | (VI) | 15 | | | |
| | [CH$_3$-dioxaborinane-phenyl(F)-phenyl(F)-CN] | (V) | 15 | | | |
| | [CH$_3$-dioxaborinane-phenyl(F)-COO-phenyl-CN] | (VI) | 15 | | | |
| | [C$_6$H$_{13}$-dioxaborinane-phenyl(F)-COO-phenyl-CN] | (VIj) | 15 | | | |
| 28. | XX | | 5 | 24.11 | −8 | 82.3 |
| | XXIII | | 5 | | | |
| | XXYI | | 5 | | | |
| | XXY | | 3 | | | |
| | YIII | | 5 | | | |
| | X | | 5 | | | |
| | XXYI | | 10 | | | |
| | XXYII | | 2 | | | |

TABLE 5-continued

| Composition No. | Liquid crystal material | | % by mass | Δε 20° C. | M.p., °C. | T$_{lim.}$, °C. |
|---|---|---|---|---|---|---|
| 1. | 2 | | 3 | 4 | 5 | 6 |
| | $C_2H_5$–[dioxaborinane]–[C$_6$H$_3$(F)]–COO–[C$_6$H$_4$]–CN | (VI) | 15 | | | |
| | $C_4H_9$–[dioxaborinane]–[C$_6$H$_3$]–[C$_6$H$_3$(F)]–CN | (V) | 15 | | | |
| 28. | $C_5H_{11}$–[dioxaborinane]–[C$_6$H$_3$(F)]–COO–[C$_6$H$_4$]–CN | (vid) | 15 | | | |
| | $C_6H_{13}$–[dioxaborinane]–[C$_6$H$_3$(F)]–COO–[C$_6$H$_4$]–CN | (vif) | 15 | | | |
| 29. | XX | | 5 | 29.15 | −5 | 75.2 |
| | XXIII | | 5 | | | |
| | XXIY | | 5 | | | |
| | XXY | | 3 | | | |
| | YIII | | 5 | | | |
| | X | | 5 | | | |
| | XXYI | | 10 | | | |
| | XXYII | | 2 | | | |
| | $C_3H_7$–[dioxaborinane]–[C$_6$H$_4$]–COO–[C$_6$H$_3$(F)]–CN | (VI$_n$) | 15 | | | |
| | $C_4H_9$–[dioxaborinane]–[C$_6$H$_4$]–COO–[C$_6$H$_3$(F)]–CN | (VIe) | 15 | | | |
| | $C_5H_{11}$–[dioxaborinane]–[C$_6$H$_4$]–[C$_6$H$_3$(F)]–CN | (V) | 15 | | | |
| | $C_6H_{13}$–[dioxaborinane]–[C$_6$H$_4$]–[C$_6$H$_3$(F)]–CN | (V) | 15 | | | |
| 30. | XX | | 5 | 54.27 | −10 | 82.6 |
| | XXIII | | 5 | | | |
| | XXIY | | 5 | | | |
| | XXY | | 3 | | | |
| | YIII | | 5 | | | |
| | X | | 5 | | | |
| | XXYI | | 10 | | | |
| | XXYII | | 2 | | | |

TABLE 5-continued

| Composition No. | Liquid crystal material | | % by mass | Δε 20° C. | M.p., °C. | T$_{lim.}$, °C. |
|---|---|---|---|---|---|---|
| 1. | 2 | | 3 | 4 | 5 | 6 |
|  | C$_3$H$_7$—[dioxaborinane]—[phenyl-F]—COO—[phenyl-F]—CN | (VI$_j$) | 15 | | | |
|  | C$_4$H$_9$—[dioxaborinane]—[phenyl-F]—COO—[phenyl-F]—CN | (VI$_o$) | 15 | | | |
|  | C$_5$H$_{11}$—[dioxaborinane]—[phenyl-F]—[phenyl-F]—CN | (V) | 15 | | | |
|  | C$_6$H$_{13}$—[dioxaborinane]—[phenyl-F]—COO—[phenyl-F]—CN | (VIV) | 15 | | | |
| 31. | C$_5$H$_{11}$—[cyclohexyl]—[pyridyl]—CN | (XXVIII) | 20.53 | 32.15 | −2 | 96.2 |
|  | C$_7$H$_{15}$—[cyclohexyl]—[pyridyl]—CN | (XXIX) | 3 | | | |
| 31. | C$_5$H$_{11}$—[cyclohexyl]—[pyridyl]—CN | (XXX) | 3 | | | |
|  | C$_3$H$_7$—[cyclohexyl]—[pyridyl]—CN | (XXXI) | 3 | | | |
|  | C$_3$H$_7$—[cyclohexyl]—[phenyl]—OC$_4$H$_9$ | (XXXII) | 3 | | | |
|  | C$_3$H$_7$—[cyclohexyl]—[phenyl]—OC$_2$H$_5$ | (XVIII) | 5 | | | |
|  | C$_3$H$_7$—[cyclohexyl]—[phenyl]—C$_2$H$_5$ | (XIX) | 5 | | | |

TABLE 5-continued

| Composition No. | Liquid crystal material | | % by mass | Δε 20° C. | M.p., °C. | T$_{lim.}$, °C. |
|---|---|---|---|---|---|---|
| 1. | 2 | | 3 | 4 | 5 | 6 |
| | C$_3$H$_7$—[dioxaborinane]—[Ph]—COO—[Ph]—CN (with F on first Ph) | (VIa) | 15 | | | |
| | C$_2$H$_5$—[dioxaborinane]—[Ph]—[Ph]—CN (with Cl) | (V) | 15 | | | |
| | CH$_3$—[dioxaborinane]—[Ph]—[Ph]—CN (with Cl) | (V) | 15 | | | |
| | C$_6$H$_{13}$—[dioxaborinane]—[Ph]—COO—[Ph]—CN (with F) | (VIj) | 15 | | | |
| 31. | C$_7$H$_{15}$—[dioxaborinane]—[Ph]—[Ph]—CN (with F) | (V) | 15 | | | |
| 32. | XXYIII | | 3 | 32.14 | −7 | 93.2 |
| | XXIX | | 3 | | | |
| | XXX | | 3 | | | |
| | XXXI | | 3 | | | |
| | XXXII | | 3 | | | |
| | XYIII | | 5 | | | |
| | XIX | | 5 | | | |
| | C$_3$H$_7$—[dioxaborinane]—[Ph]—COO—[Ph]—CN (with F) | (VIh) | 15 | | | |
| | C$_4$H$_9$—[dioxaborinane]—[Ph]—[Ph]—CN (with Cl, Cl) | (V) | 15 | | | |
| | CH$_3$—[dioxaborinane]—[Ph]—COO—[Ph]—CN (with F, F) | (VI) | 15 | | | |
| | C$_6$H$_{13}$—[dioxaborinane]—[Ph]—COO—[Ph]—CN (with F) | (VIj) | 15 | | | |

TABLE 5-continued

| Composition No. 1. | Liquid crystal material 2. | | % by mass 3 | Δε 20° C. 4 | M.p., °C. 5 | T_lim., °C. 6 |
|---|---|---|---|---|---|---|
| | C₇H₁₅—[dioxaborinane]—[phenyl(F)]—COO—[phenyl]—CN | (VIg) | 15 | | | |
| 33. | XXYIII | | 3 | 32.27 | −8 | 84.5 |
| | XXIX | | 3 | | | |
| | XXX | | 3 | | | |
| | XXXI | | 3 | | | |
| | XXXII | | 3 | | | |
| | XYIII | | 5 | | | |
| | XIX | | 5 | | | |
| | C₃H₇—[dioxaborinane]—[phenyl(F)]—COO—[phenyl]—CN | (VIa) | 15 | | | |
| | C₄H₉—[dioxaborinane]—[phenyl(F)]—COO—[phenyl]—CN | (VIc) | 15 | | | |
| | C₅H₁₁—[dioxaborinane]—[phenyl(F)]—COO—[phenyl]—CN | (vid) | 15 | | | |
| | C₆H₁₃—[dioxaborinane]—[phenyl(F)]—COO—[phenyl]—CN | (VIf) | 15 | | | |
| | C₇H₁₅—[dioxaborinane]—[phenyl(F)]—COO—[phenyl(F)]—CN | (VIw) | 15 | | | |
| 34. | C₅H₁₁—[cyclohexyl]—[pyridyl]—CN | (XXVIII) | 3 | 27.87 | −10 | 98.1 |
| 34. | C₇H₁₅—[cyclohexyl]—[pyridyl]—CN | (XXIX) | 3 | | | |
| | C₅H₁₁—[cyclohexyl]—[pyridyl]—CN | (XXX) | 3 | | | |

TABLE 5-continued
| Composition No. 1. | Liquid crystal material 2. | | % by mass 3 | Δε 20° C. 4 | M.p., °C. 5 | T$_{lim.}$, °C. 6 |
|---|---|---|---|---|---|---|
| | 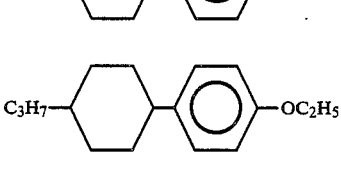 | (XXXI) | 3 | | | |
| | 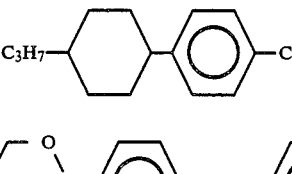 | (XXXII) | 3 | | | |
| | 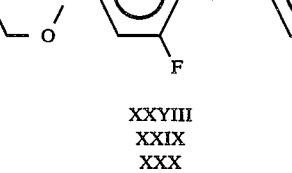 | (XVIII) | 5 | | | |
| | 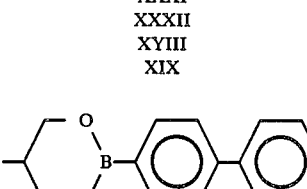 | (XIX) | 5 | | | |
| | 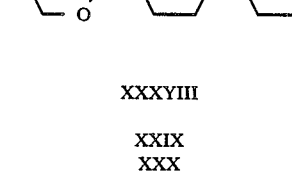 | (VId) | 75 | | | |
| 35. | XXYIII | | 3 | 15.07 | 1 | 84.1 |
| | XXIX | | 3 | | | |
| | XXX | | 3 | | | |
| | XXXI | | 3 | | | |
| | XXXII | | 3 | | | |
| | XYIII | | 5 | | | |
| | XIX | | 5 | | | |
| | 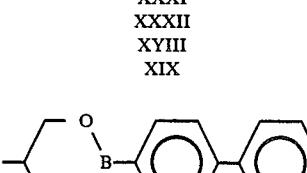 | (V) | 75 | | | |
| 36. | XXXYIII | | 3 | 22.6 | 0 | 77.2 |
| | XXIX | | 3 | | | |
| | XXX | | 3 | | | |
| | XXXI | | 3 | | | |
| | XXXII | | 3 | | | |
| | XYIII | | 5 | | | |
| | XIX | | 5 | | | |
| | 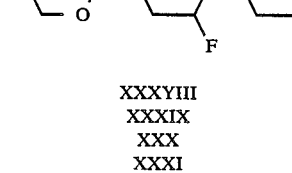 | (V) | 75 | | | |
| 37. | XXXYIII | | 3 | 21.57 | −8 | 91.7 |
| | XXXIX | | 3 | | | |
| | XXX | | 3 | | | |
| 37. | XXXI | | 3 | | | |
| | XXXII | | 3 | | | |
| | XYIII | | 5 | | | |
| | XXI | | 5 | | | |

TABLE 5-continued

| Composition No. | Liquid crystal material | | % by mass | Δε 20° C. | M.p., °C. | T$_{lim.}$, °C. |
|---|---|---|---|---|---|---|
| 1. | 2 | | 3 | 4 | 5 | 6 |
| | 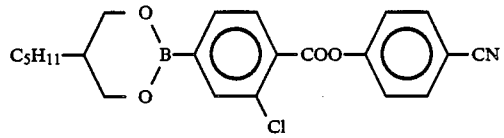 | (VIe) | 75 | | | |
| 38. | XXXYIII<br>XXXIX<br>XXX<br>XXXI<br>XXXII<br>XYIII<br>XXI | | 3<br>3<br>3<br>3<br>3<br>5<br>5 | 25.11 | −9 | 91.7 |
| | 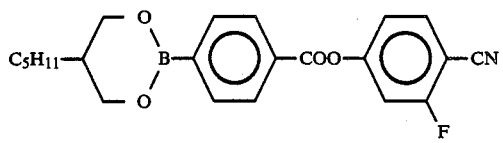 | (VIp) | 75 | | | |
| 39. | XXYIII<br>XXIX<br>XXX<br>XXXI<br>XXXII<br>XYIII | | 3<br>3<br>3<br>3<br>3<br>5 | 24.12 | −3 | 95.2 |
| 39. | XIX | | 5 | | | |
| | 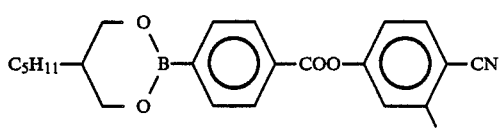 | (VIq) | 75 | | | |
| 40. | XXYIII<br>XXIX<br>XXX<br>XXXI<br>XXXII<br>XYIII<br>XIX | | 3<br>3<br>3<br>3<br>3<br>5<br>5 | 58.43 | −11 | 100.8 |
| | 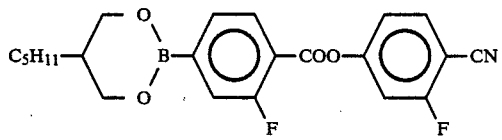 | | | | | |
| 41. | XXYII<br>XXXIX<br>XXX<br>XXXI<br>XXXII<br>XYIII<br>XIX | | 3<br>3<br>3<br>3<br>3<br>5<br>5 | 27.14 | 1 | 68.6 |
| | 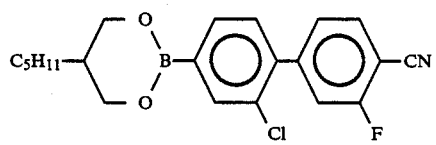 | (V) | 75 | | | |
| 42. | XXYIII<br>XXIX<br>XXX<br>XXXI<br>XXXII<br>XYIII<br>XIX | | 3<br>3<br>3<br>3<br>3<br>3<br>5 | 41.13 | +3 | 77.1 |

TABLE 5-continued

| Composition No. | Liquid crystal material | | % by mass | Δε 20° C. | M.p., °C. | T$_{lim.}$, °C. |
|---|---|---|---|---|---|---|
| 1. | 2 | | 3 | 4 | 5 | 6 |
| | C$_5$H$_{11}$–[dioxaborinane]–[Ph(F)]–COO–[Ph(Cl)]–CN | (VIx) | 75 | | | |
| 43. | XXXIII | | 3 | 21.14 | +6 | 75.8 |
| | XXIX | | 3 | | | |
| | XXX | | 3 | | | |
| | XXXI | | 3 | | | |
| | XXXII | | 3 | | | |
| | XYIII | | 5 | | | |
| | XIX | | 5 | | | |
| | C$_5$H$_{11}$–[dioxaborinane]–[Ph(Cl)]–[Ph(Cl)]–CN | (V) | 75 | | | |
| 44. | C$_5$H$_{11}$–[pyrimidine]–[Ph]–CN | (XXXIII) | 8 | 5.41 | −27 | 79.4 |
| 44. | C$_5$H$_{11}$–[pyridine]–[Ph]–CN | (XXIII) | 12 | | | |
| | C$_5$H$_{11}$–[Cy]–CH$_2$CH$_2$–[Ph]–CN | (XXXIV) | 17 | | | |
| | C$_3$H$_7$–[Cy]–CH$_2$CH$_2$–[Ph]–OC$_2$H$_5$ | (XXVI) | 13 | | | |
| | C$_5$H$_{11}$–[Cy]–CH$_2$CH$_2$–[Ph]–OC$_2$H$_5$ | (XXXV) | 10 | | | |
| | C$_3$H$_7$–[Cy]–[Ph]–C$_2$H$_5$ | (XIX) | 10 | | | |
| | C$_3$H$_7$–[Cy]–[Ph]–[pyridine]–C$_2$H$_5$ | (XXXVI) | 7 | | | |
| | C$_5$H$_{11}$–[Cy]–[Ph]–[pyridine]–C$_2$H$_5$ | (XXXVII) | 7 | | | |

TABLE 5-continued

| Composition No. | Liquid crystal material | % by mass | Δε 20° C. | M.p., °C. | T$_{lim.}$, °C. |
|---|---|---|---|---|---|
| 1. | 2 | 3 | 4 | 5 | 6 |
| | C$_5$H$_{11}$—[Cy]—[Ph-N]—[Ph]—CN (XXXVIII) | 8 | | | |
| | C$_5$H$_{11}$—[Cy]—[Ph]—[Ph]—[Cy]—C$_5$H$_{11}$ (XXXIX) | 5 | | | |
| 44. | C$_5$H$_{11}$—[dioxaborinane]—[Ph]—[Ph(F)]—CN (V) | 3 | | | |
| 45. | XXXIII | 8 | 6.13 | −26 | 75.2 |
| | XXIII | 12 | | | |
| | XXXIY | 17 | | | |
| | XXYI | 13 | | | |
| | XXXY | 10 | | | |
| | XIX | 10 | | | |
| | XXXYI | 7 | | | |
| | XXXYII | 7 | | | |
| | XXXYIII | 8 | | | |
| | XXXIX | 5 | | | |
| | C$_5$H$_{11}$—[dioxaborinane]—[Ph(F)]—[Ph(F)]—CN (V) | 3 | | | |
| 46. | XXXIII | 8 | 6.23 | −29 | 80.1 |
| | XXIII | 12 | | | |
| | XXXIY | 17 | | | |
| | XXYI | 13 | | | |
| | XXXY | 10 | | | |
| | XIX | 10 | | | |
| | XXXYI | 7 | | | |
| | XXXYII | 7 | | | |
| 46. | XXXYIII | 8 | | | |
| | XXXIX | 5 | | | |
| | C$_5$H$_{11}$—[dioxaborinane]—[Ph(F)]—COO—[Ph]—CN (VId) | 3 | | | |
| 47. | XXXIII | 8 | 8.16 | −38 | 81.4 |
| | XXIII | 12 | | | |
| | XXXIY | 17 | | | |
| | XXYI | 13 | | | |
| | XXXY | 10 | | | |
| | XIX | 10 | | | |
| | XXXYI | 7 | | | |
| | XXXYII | 7 | | | |
| | XXXYIII | 8 | | | |
| | XXXIX | 5 | | | |
| | C$_5$H$_{11}$—[dioxaborinane]—[Ph(F)]—COO—[Ph(F)]—CN | | | | |

TABLE 5-continued

| Composition No. | Liquid crystal material | | % by mass | Δε 20° C. | M.p., °C. | $T_{lim.}$, °C. |
|---|---|---|---|---|---|---|
| 1. | 2. | | 3 | 4 | 5 | 6 |
| 48. | C₅H₁₁—[pyrazine]—⌬—CN | (XXXIII) | 8 | 6.87 | −34 | 79.3 |
|  | C₅H₁₁—[pyridine]—⌬—CN | (XXIII) | 12 | | | |
| 48. | C₅H₁₁—⟨cyclohexyl⟩—CH₂CH₂—⌬—CN | (XXXIV) | 17 | | | |
|  | C₃H₇—⟨cyclohexyl⟩—CH₂CH₂—⌬—OC₂H₅ | (XXVI) | 13 | | | |
|  | C₅H₁₁—⟨cyclohexyl⟩—CH₂CH₂—⌬—OC₂H₅ | (XXXV) | 10 | | | |
|  | C₃H₇—⟨cyclohexyl⟩—⌬—C₂H₅ | (XIX) | 10 | | | |
|  | C₃H₇—⟨cyclohexyl⟩—⌬—[pyridine]—C₂H₅ | (XXXVI) | 7 | | | |
|  | C₅H₁₁—⟨cyclohexyl⟩—⌬—[pyridine]—C₂H₅ | (XXXVII) | 7 | | | |
|  | C₅H₁₁—⟨cyclohexyl⟩—[pyridine]—⌬—CN | (XXXVIII) | 8 | | | |
|  | C₅H₁₁—⟨cyclohexyl⟩—⌬—⌬—⟨cyclohexyl⟩—C₅H₁₁ | (XXXIX) | 5 | | | |
|  | C₅H₁₁—[dioxaborinane]—⌬(Cl)—COO—⌬(F)—CN | (VIt) | 3 | | | |
| 49. | XXXIII | | 10 | 5.02 | −34 | 78.2 |
|  | XXIII | | 12 | | | |
|  | XXXIV | | 17 | | | |
|  | XXVI | | 13 | | | |
|  | XXXV | | 10 | | | |
|  | XIX | | 10 | | | |
|  | XXXVI | | 7 | | | |
|  | XXXVII | | 7 | | | |
|  | XXXVIII | | 5 | | | |

TABLE 5-continued
| Composition No. | Liquid crystal material | | % by mass | Δε 20° C. | M.p., °C. | T_lim., °C. |
|---|---|---|---|---|---|---|
| 1. | 2 | | 3 | 4 | 5 | 6 |
| | XXXIX | | 5 | | | |
| | 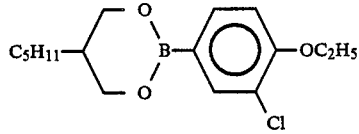 | (II) | 4 | | | |
| 50. | 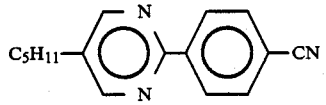 | (XXXIII) | 10 | 5.08 | −29 | 82.2 |
| | 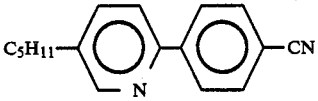 | (XXIII) | 12 | | | |
| | 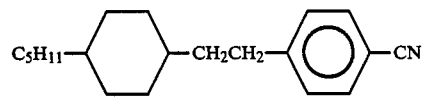 | (XXXIV) | 17 | | | |
| | 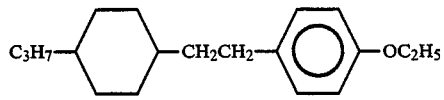 | (XXV() | 13 | | | |
| 50. | 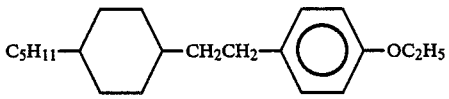 | (XXXV) | 10 | | | |
| | 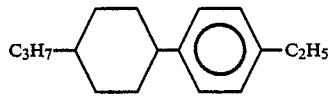 | (XIX) | 10 | | | |
| |  | (XXXVI) | 7 | | | |
| | 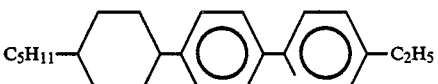 | (XXXVII) | 7 | | | |
| | 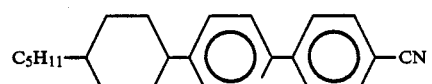 | (XXXVIII) | 5 | | | |
| |  | (XXXIX) | | | | |
| | 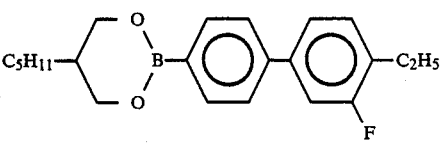 | (IV) | 1 | | | |

TABLE 5-continued

| Composition No. | Liquid crystal material | | % by mass | Δε 20° C. | M.p., °C. | T$_{lim}$, °C. |
|---|---|---|---|---|---|---|
| 1. | 2 | | 3 | 4 | 5 | 6 |
| 51. | XXXIII | | 10 | 5.06 | −33 | 76.1 |
| | XXIII | | 12 | | | |
| | XXXIY | | 17 | | | |
| | XXYI | | 13 | | | |
| 51. | XXXY | | 10 | | | |
| | XIX | | 10 | | | |
| | XXXYI | | 7 | | | |
| | XXXYII | | 7 | | | |
| | XXXYIII | | 5 | | | |
| | XXXIX | | 5 | | | |
| | $C_5H_{11}$—[structure with B, O, OC$_4$H$_9$, F] | (II) | 4 | | | |
| 52. | XXXIII | | 10 | 5.12 | −30 | 80.3 |
| | XXIII | | 12 | | | |
| | $C_5H_{11}$—⟨cyclohexyl⟩—CH$_2$CH$_2$—⟨phenyl⟩—CN | (XXXIV) | 17 | | | |
| | $C_3H_7$—⟨cyclohexyl⟩—CH$_2$CH$_2$—⟨phenyl⟩—OC$_2$H$_5$ | (XXVI) | 13 | | | |
| | $C_5H_{11}$—⟨cyclohexyl⟩—CH$_2$CH$_2$—⟨phenyl⟩—OC$_2$H$_5$ | (XXXV) | 10 | | | |
| | $C_3H_7$—⟨cyclohexyl⟩—⟨phenyl⟩—C$_2$H$_5$ | (XIX) | 10 | | | |
| 52. | $C_3H_7$—⟨cyclohexyl⟩—⟨phenyl⟩—⟨pyridyl-N⟩—C$_2$H$_5$ | (XXXVI) | 7 | | | |
| | $C_5H_{11}$—⟨cyclohexyl⟩—⟨phenyl⟩—⟨pyridyl-N⟩—C$_2$H$_5$ | (XXXVII) | 7 | | | |
| | $C_5H_{11}$—⟨cyclohexyl⟩—⟨pyridyl-N⟩—⟨phenyl⟩—CN | (XXXVIII) | 5 | | | |
| | $C_5H_{11}$—⟨cyclohexyl⟩—⟨phenyl⟩—⟨phenyl⟩—⟨phenyl⟩—$C_5H_{11}$ | (XXXIX) | 5 | | | |

TABLE 5-continued

| Composition No. 1. | Liquid crystal material 2 | | % by mass 3 | Δε 20° C. 4 | M.p., °C. 5 | T$_{lim.}$, °C. 6 |
|---|---|---|---|---|---|---|
| | C$_5$H$_{11}$—[dioxaborinane]—[phenyl(Cl)]—[phenyl]—C$_2$H$_5$ | (IV) | 4 | | | |
| 53. | XXXIII | | 10 | 5.14 | −29 | 80.9 |
| | XXIII | | 12 | | | |
| | XXXIV | | 17 | | | |
| | XXVI | | 13 | | | |
| | XXXV | | 10 | | | |
| | XIX | | 10 | | | |
| | XXXVI | | 7 | | | |
| | XXXVII | | 7 | | | |
| | XXXXVIII | | 5 | | | |
| | XXXIX | | 5 | | | |
| 53. | C$_5$H$_{11}$—[dioxaborinane]—[phenyl(F)]—[cyclohexyl(F)]—C$_2$H$_5$ | (IV) | 4 | | | |
| 54. | XXXIII | | 10 | 5.03 | −31 | 79.4 |
| | XXIII | | 12 | | | |
| | XXXIV | | 17 | | | |
| | XXVI | | 13 | | | |
| | XXXV | | 10 | | | |
| | XIX | | 10 | | | |
| | XXXVI | | 7 | | | |
| | XXXVII | | 7 | | | |
| | XXXVIII | | 5 | | | |
| | XXXIX | | 3 | | | |
| | C$_5$H$_{11}$—[dioxaborinane]—[phenyl(F)]—[phenyl(Cl)]—C$_3$H$_7$ | (IV) | 3 | | | |
| | C$_4$H$_9$—[cyclohexyl]—COO—[phenyl]—OC$_6$H$_{13}$ | (LC) | 3 | | | |

EXAMPLE 7

A liquid crystal material of composition 55.1–55.2, comprising trans-4-propyl-4(4'-ethoxyphenyl)cyclohexane (XVIII), 4-hexylhydrophenyl ester of trans-4-butylcyclohexanecarboxylic acid (LC), 2-(4-ethoxy-3-fluorophenyl)-5-pentyl-1,3,2-dioxaborinane (II), 2-/4'-(4-cyano-3-fluorophenylhydroxycarbonyl)-3'-fluorophenyl/-5-pentyl-1,3,2-dioxaborinane (VIs), was prepared similarly to the liquid crystal material of composition 1, as in Example 6.

The content of components in the liquid crystal material of composition 55.1–55.2 and its electrooptical parameters measured at room temperature are presented in Table 6.

TABLE 6

| Composition Nos. | Content of components in liquid crystal material, percent by mass | | | | U$_{10}$ (V) | U$_{50}$ (V) | U$_{90}$ (V) | P$_{50}$ | τON (ms) | τOFF (ms) |
|---|---|---|---|---|---|---|---|---|---|---|
| | XVIII | LC | II | VIs | | | | | | |
| 55.1 | 30 | 55 | 5 | 10 | 2.05 | 2.26 | 2.57 | 0.102 | 55 | 90 |
| 55.2 | 25 | 55 | 10 | 10 | 2.00 | 2.21 | 2.51 | 0.105 | 50 | 100 |

EXAMPLE 8

A liquid crystal material of composition 56.1–56.5, comprising trans-4-propyl-(4'-ethoxyphenyl)cyclohexane (XVIII), 4-hexylhydroxyphenyl ester of trans-4-butylcyclohexacarboxylic acid (LC), 2-/4'-(4-cyano-3-fluorophenylhydroxycarbonyl)-3'-fluorophenyl/-5- pentyl-1,3,2-dioxaborinane (VIs), was prepared similarly to the liquid crystal material of composition 1, as in Example 6.

The content of the components in the liquid crystal material of composition 56.1–56.5 and is electrooptical parameters measured at room temperature are presented in Table 7.

TABLE 7

| Composition No. | | Content of components in liquid crystal material, % by mass | | | $\frac{1}{U_{90}} \cdot \left(\frac{\Delta U}{\Delta T}\right)$ 100% | $U_{10}$ (V) | $U_{50}$ (V) | $U_{90}$ (V) | $P_{50}$ | $\tau_{ON}$ (ms) | $\tau_{OFF}$ (ms) | $\Delta n$ |
|---|---|---|---|---|---|---|---|---|---|---|---|---|
| | | XVIII | LC | VI | | | | | | | | |
| | 1 | 2 | 3 | 4 | 5 | 6 | 7 | 8 | 9 | 10 | 11 | 12 |
| 56. | 1 | 36 | 54 | 10 | 0.186 | 2.10 | 2.325 | 2.67 | 0.107 | 50 | 100 | 0.0833 |
| 56. | 2 | 42 | 48 | 10 | 0.19 | 2.16 | 2.39 | 2.72 | 0.III | 52 | 100 | 0.0842 |
| 56. | 3 | 38 | 52 | 10 | 0.196 | 2.13 | 2.36 | 2.69 | 0.115 | 52 | 100 | 0.0839 |
| 54. | 4 | 40 | 55 | 5 | 0.201 | 2.26 | 2.52 | 2.89 | 0.115 | 54 | 100 | 0.0867 |
| 55. | 5 | 45 | 50 | 5 | 0.207 | 2.3 | 2.57 | 2.96 | 0.117 | 55 | 100 | 0.0873 |

EXAMPLE 9

A liquid crystal material of composition 57.1–57.8, comprising trans-4-propyl-(4-ethoxyphenyl)cyclohexane (XVIIII), 4-hexylhydroxyphenyl ester of trans-4-butylcyclohexanecarboxylic acid (LC), 4-ethoxyphenyl ester of trans-4-butylcyclohexanecarboxylic acid (VIII), 2-/4'-(4-cyano-3-fluorophenylhydroxycarbonyl)-3'-fluorophenyl/-5-penyl-1,3,2-dioxaborinane (VIi), 2-/4'-(4-cyano-3-fluorophenylhydroxycarbonyl)-3'-chlorophenyl/-5-pentyl-1,3,2-dioxaborinane (VIt), was prepared similarly to the liquid crystal material of composition 1, as in Example 6.

The content of the components in the liquid crystal material of composition 57.1–57.8 and its electrooptical parameters measured at room temperature are presented in Table 8.

$$\frac{1}{U_{90}} \left(\frac{\Delta U}{\Delta T}\right) \cdot 100\%$$

is the temperature drift, where $\Delta U$ is the difference between the threshold voltages of the mixture at 50° C. and 10° C.; $\Delta T$ is the temperature variation from 10° C. to 50° C. ($\Delta T = 50° - 10° = 40°$), $U_{90}$ being measured at 20° C.

The ON and OFF periods are measured at U=3 V.

Thus, as is seen from Examples 1–9 and Tables 1–8, the compounds of the formula (I)–(VI), according to the invention, as compared to the compounds disclosed in Applications JP, A, No. 61-109792, JP, A, No. 61-83190, feature lower values of the nematic phase formation temperatures and higher values of the positive anisotropy of permittivity. These properties allow the provision, by using the compounds of the present invention, of liquid crystal materials featuring low values of the threshold voltage and saturation voltage, a steep voltage-contrast characteristic, short ON and OFF periods, and operating in the range of low temperatures.

TABLE 8

| Composition No. | | Content of components in liquid crystal material, % by mass | | | | | | $\frac{1}{U_{90}} \cdot \left(\frac{\Delta U}{\Delta T}\right)$ 100% | $U_{10}$ (V) | $U_{50}$ (V) | $U_{90}$ (V) | $P_{50}$ | $\tau_{ON}$ (ms) | $\tau_{OFF}$ (ms) | $\Delta n$ |
|---|---|---|---|---|---|---|---|---|---|---|---|---|---|---|---|
| | | VIII | XVIII | LC | VIs | VIi | Vit | | | | | | | | |
| | 1 | 2 | 3 | 4 | 5 | 6 | 7 | 8 | 9 | 10 | 11 | 12 | 13 | 14 | 15 |
| 57. | 1 | 22 | 27 | 41 | 10 | — | — | 0.23 | 2.05 | 2.27 | 2.62 | 0.107 | 50 | 80 | 0.0801 |
| 57. | 2 | 24 | 28 | 43 | 5 | — | — | 0.241 | 2.99 | 3.34 | 3.95 | 0.117 | 52 | 80 | 0.0850 |
| 57. | 3 | 20 | 24 | 48 | 8 | — | — | 0.236 | 2.65 | 2.95 | 3.30 | 0.114 | 52 | 80 | 0.0841 |
| 57. | 4 | 22 | 27 | 41 | — | 10 | — | 0.223 | 2.09 | 2.32 | 2.7 | 0.III | 33 | 42 | 0.0838 |
| 57. | 5 | 24 | 28 | 43 | — | 5 | — | 0.229 | 2.39 | 2.7 | 3.12 | 0.129 | 35 | 42 | 0.0873 |
| 57. | 6 | 20 | 24 | 48 | — | 8 | — | 0.228 | 2.3 | 2.58 | 3.08 | 0.121 | 35 | 42 | 0.0861 |
| 57. | 7 | 22 | 27 | 41 | — | — | 10 | 0.228 | 2.12 | 2.35 | 2.72 | 0.108 | 60 | 87 | 0.0804 |
| 57. | 8 | 24 | 28 | 43 | — | — | 5 | 0.236 | 2.6 | 2.92 | 3.4 | 0.123 | 63 | 88 | 0.0856 | where:
$U_{10}$ is the voltage at which the cell passes 10% of the light falling on it (threshold voltage)
$U_{50}$ is the voltage at which the cell passes 50% of the light falling on it
$U_{90}$ is the voltage at which the cell passes 90% of the light falling on it (saturation voltage)
$P_{50}$ is the steepness parameter ($P_{50} = U_{50} - U_{10})/U_{10}$)
$\tau_{ON}$ is the time during which the cell contrast changes from 10% to 90% (ON period)
$\tau_{OFF}$ is the time during which the cell contrast changes from 90% to 10% (OFF period)
$\Delta n$ is the optical anisotropy

We claim:
1. 2-(4,3-Disubstituted phenyl)-5-alkyl-1,3,2-dioxaborinane derivatives of the general formula

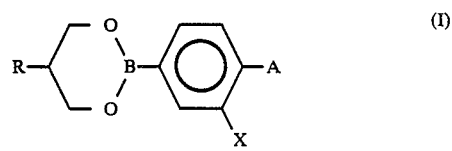

(I)

wherein A is —OR', —CN,

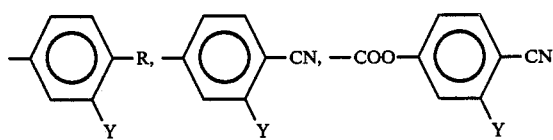

X and Y being simultaneously or independently H, F, or Cl, at least one of X and Y being other than H, R and R' standing for an alkyl radical of a normal structure, comprising from 1 to 7 carbon atoms, as components for a liquid crystal material.

2. A compound as claimed in claim 1, of the formula

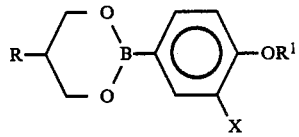

(II)

wherein X is F.

3. A compound as claimed in claim 1, of the formula

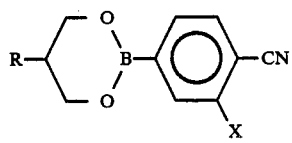

(III)

wherein X is F.

4. A compound as claimed in claim 1, of the formula

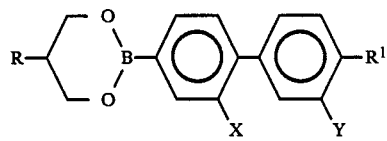

(IV)

wherein X and Y are F.

5. A compound as claimed in claim 1, of the formula

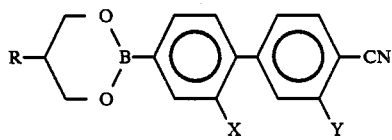

(V)

wherein X and Y are F.

6. A compound as claimed in claim 1, of the formula

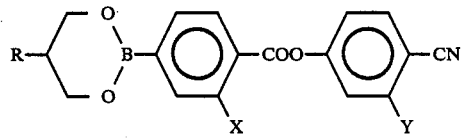

(VI)

wherein X and Y are F.

7. A liquid crystal material comprising at least two components, of which at least one is a 2-(4,3-disubstituted phenyl)-5-alkyl-1,3,2-dioxaborinane derivative of the general formula

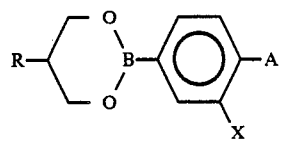

(I)

wherein A is —OR—, or —CN,

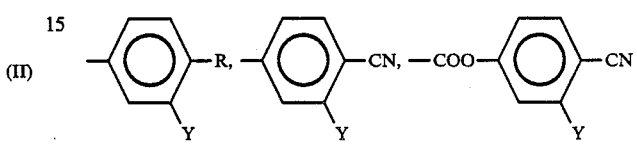

X and Y being simultaneously or independently H, F, or Cl, at least one of X and Y being other than H, R, R' standing for an alkyl radical of a normal structure, comprising from 1 to 7 carbon atoms.

8. A liquid crystal material as claimed in claim 7, which comprises at least one said compound of the formula

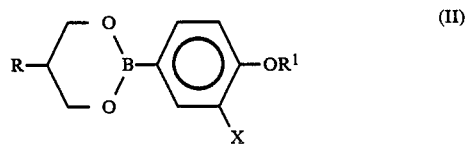

(II)

wherein X is F.

9. A liquid crystal material as claimed in claim 7, which comprises at least one said compound of the formula

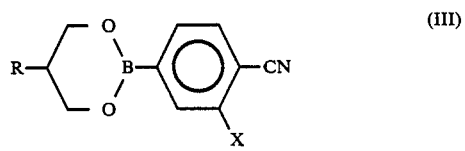

(III)

wherein X is F.

10. A liquid crystal material as claimed in claim 7, which comprises at least one said compound of the formula

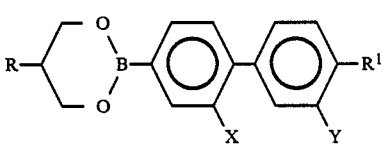

(IV)

wherein X and Y are F.

11. A liquid crystal material as claimed in claim 7, which comprises at least one said compound of the formula

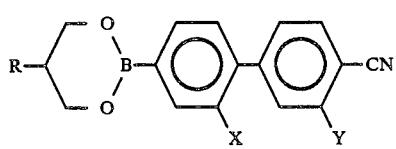
wherein Z and Y are F.
12. A liquid crystal material as claimed in claim 7, which comprises at least one said compound of the formula
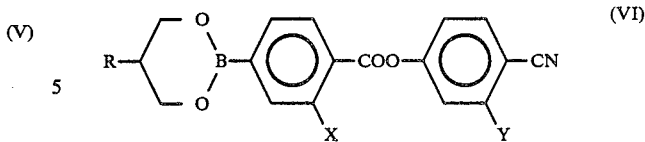
wherein X and Y are F.
13. A liquid crystal material as claimed in claim 7, wherein the content of said 2-(4,3-disubstituted phenyl)-5-alkyl-1,3,2-dioxaborinane derivative ranges from 3 to 75 percent by mass.
* * * * *